(12) United States Patent
Gfrörer et al.

(10) Patent No.: US 7,355,710 B2
(45) Date of Patent: Apr. 8, 2008

(54) OPTICAL SYSTEM AND METHOD FOR EXCITING AND MEASURING FLUORESCENCE ON OR IN SAMPLES TREATED WITH FLUORESCENT PIGMENTS

(75) Inventors: Andreas Gfrörer, Königsdorf (DE); Josef Atzler, Hallein (AT)

(73) Assignee: Tecan Trading AG, Mannedorf (CH)

( * ) Notice: Subject to any disclaimer, the term of this patent is extended or adjusted under 35 U.S.C. 154(b) by 0 days.

(21) Appl. No.: 11/559,483

(22) Filed: Nov. 14, 2006

(65) Prior Publication Data

US 2007/0086005 A1  Apr. 19, 2007

Related U.S. Application Data

(63) Continuation of application No. 10/470,154, filed as application No. PCT/CH02/00014 on Jan. 10, 2002, now Pat. No. 7,158,226.

(30) Foreign Application Priority Data

Jan. 26, 2001 (CH) ........................ 144/01

(51) Int. Cl.
*G01N 21/25* (2006.01)

(52) U.S. Cl. ..................................................... 356/417
(58) Field of Classification Search ................ 356/318, 356/417; 250/458.1
See application file for complete search history.

(56) References Cited

U.S. PATENT DOCUMENTS 5,459,325 A * 10/1995 Hueton et al. ........... 250/458.1
2002/0060791 A1 * 5/2002 Stumbo et al. ............. 356/317

* cited by examiner

*Primary Examiner*—Kara Geisel
(74) *Attorney, Agent, or Firm*—Notaro & Michalos P.C.

(57) ABSTRACT

An optical system for exciting and measuring fluorescence of samples has a first laser; a deflection element; a mirror; and an optic fixed in relation to one another. A unit is linearly movable back and forth along the optical axis and is mechanically connected to an oscillating linear drive. The optic acts as a collimator and the mirror acts to deflect the collimated light diametrically opposite to the bundled light of the laser. A table for receiving sample holders for samples; an optical arrangement for imaging a second focal point; an aperture plate in the second focal point; a first spectral filter; and a first detector are parts of the optical system and a focusing beam of the light emitted by the laser and is deflected by the deflection element toward the mirror.

37 Claims, 2 Drawing Sheets

OPTICAL SYSTEM AND METHOD FOR EXCITING AND MEASURING FLUORESCENCE ON OR IN SAMPLES TREATED WITH FLUORESCENT PIGMENTS

RELATED APPLICATION DATA

This application is a continuation application of U.S. Ser. No. 10/470,154, filed on Nov. 24, 2003 now U.S. Pat. No. 7,158,226 which is a National Stage Application of PCT/CH02/00014, filed on Jan. 10, 2002, and which claims priority of the Swiss Application No. CH 0144/01, filed on Jan. 26, 2001, the entire disclosures of which are incorporated herein by reference.

TECHNICAL FILED AND BACKGROUND OF THE INVENTION

The present invention relates to an optical system for exciting and measuring fluorescence on or in samples treated with fluorescent pigments. Such optical systems are known, for example, as scanning light microscopes.

Scanning light microscopes have been known for several decades. Their functional principal is based on a light beam being concentrated to a small point of light (the first focal point) on a sample. The sample and this point of light are mutually moved in such a way that a specific area of the sample is scanned (rasterized) by the point of light. The light which penetrates the sample or is reflected by it and/or the fluorescence triggered on or in the sample during the scanning is therefore referred to as "light originating from the sample" and is measured by one or more photodetectors. An enlarged image is produced in that an original measurement point is assigned a specific area on an image of the sample. In principle, such a scanning light microscope therefore includes:

a light source, which produces a light beam;
a sample holder for holding the sample;
an optic for producing a first focal point on the sample;
an optical arrangement for imaging a second focal point using the light which shines through the sample and/or is reflected by the sample and/or which represents fluorescence triggered on or in the sample;
a photodetector for measuring the intensity of the second focal point; and
a scanning mechanism for mutual movement of the sample and first focal point.

In a conventional scanning light microscope, the light beam is deflected in the direction of the two spatial axes X and Y to illuminate the sample. This procedure hides the disadvantage that the angle of incidence on the sample of the light refracted by the projective lens varies and produces an aberration in the imaging of the sample light by the objective lens. This aberration may be corrected through an appropriate construction of the objective lens. such a lens disadvantageously makes the optic more costly and simultaneously has a limiting effect in regard to the light collecting efficiency and operating distance.

According to U.S. Pat. No. 5,081,350, this problem is solved in that a device is disclosed therein using which the sample is scanned by a light beam. In this case, the device for illuminating the sample and the device for measuring the signal coming from the sample are mounted on a unit which is movable back and forth. The sample is mounted on a sample table movable perpendicularly to this oscillation in this case, so that scanning of the sample is possible with a constant angle of incidence of the illumination. Because, especially for the application of a rapid scanning method, the light source is preferably to be positioned outside the movable part of the scanning light microscope, in this case the use of glass fiber waveguides is suggested, which optically connect the light source to the projective. However, there is the danger that this glass fiber cable may be damaged by the frequent and rapid back and forth movement.

An improved device according to the species is known from U.S. Pat. No. 5,260,569, which solves the problems of the related art described above in that a scanning light microscope is suggested therein which, as a light source, includes a laser, a mirror for deflecting the light, coming out of the laser and incident parallel to an optical axis on the mirror, in the direction of a sample, a deflection element for deflecting this light onto this mirror, an optic for producing a first focal point, a unit, including the mirror and the optic, in which linearly movable back and are positioned fixed in relation to one another, which is linearly movable back and forth along the optical axis, an oscillating linear drive which is mechanically connected to this unit, a sample table, movable at least in the direction of the X and Z spatial axes, for aligning the sample in relation to the first focal point, an optical arrangement for imaging a second focal point using the light originating from the sample, an aperture plate, positioned in the second focal point, for masking light originating from the sample which meets this aperture plate at a distance greater than a specific distance, a spectral filter for selecting a component of the light originating from the sample which passes through the aperture plate, and a detector for measuring the intensity of the light originating from the sample which passes through the aperture plate and is selected by the spectral filter. The optic is additionally implemented as a collimator for the light originating from the sample and the mirror is additionally implemented for deflecting this collimated light diametrically opposite to the direction of incidence of the light from the laser and parallel to the optical axis.

U.S. Pat. No. 5,260,569 also discloses a scanning light microscope in which the light emitted by a light source is aligned in parallel using a collimating lens acting as a part of the projective. The collimated light propagates in the direction parallel to the scanning direction of the microscope. Therefore, the collimated light beam—independently of the actual position of the unit movable back and forth—is always incident from the same direction on the mirror which is fixed in the unit movable back and forth. This has the consequence that the light beam is always reflected by the mirror onto the sample in the same direction and in collimated form. This collimated light is, after a 90° reflection on the mirror, bundled into a first focal point using a further projective lens which is also fixed in the unit movable back and forth. Therefore, the scanning or rasterizing of the sample may be performed using the unit movable back and forth and using the light of a light source which is attached to the unit movable back and forth. However, the attachment of the light source and photodetector outside the unit movable back and forth is preferable, so that this unit may be made simpler and lighter—to allow more rapid scanning.

SUMMARY OF THE INVENTION

The object of the present invention is to suggest an alternative optical system and/or an alternative optical method which opens up addition possibilities for a simpler, more flexible system construction and/or system use and essentially has the advantages of the related art.

According to a first aspect, this object is achieved by an optical system for exciting and measuring fluorescence on or in samples treated using fluorescent pigments, comprising:
- at least one first laser which emits light of a first wavelength to excite first fluorescent pigments, so that these first fluorescent pigments emit light of a second wavelength;
- a mirror, for deflecting the light of the first wavelength, which comes out of the first laser and is incident on the mirror parallel to an optical axis, in the direction of a sample;
- a deflection element for deflecting the light from the first laser onto this mirror;
- an optic, for producing a first focal point for the light of the first wavelength, which is incident from the first laser and is deflected by the mirror;
- a unit, which includes the mirror and optic, the mirror and optic being positioned fixed in relation to one another in the unit and this unit being positioned so it is linearly movable back and forth along the optical axis and being mechanically connected to an oscillating linear drive, the optic additionally being implemented as a collimator for the light of the second wavelength emitted by the first fluorescent pigment and the mirror additionally being implemented for deflecting this collimated light diametrically opposite to the direction of incidence of the light of the first wavelength and parallel to the optical axis;
- a table, movable at least in the direction of the X and Z spatial axes, for receiving sample holders for samples treated using at least one first fluorescent pigment and for aligning the sample in relation to the first focal point;
- an optical arrangement for imaging a second focal point using the light of the second wavelength, which is emitted by the first fluorescent pigment, collimated by the optic, and deflected by the mirror;
- an aperture plate, positioned in the second focal point, for masking light of the second wavelength, which is incident on this aperture plate at a distance from the focal point greater than a specific distance;
- a first spectral filter for selecting a component of the light of the second wavelength passing through the aperture plate; and
- a first detector for measuring the intensity of the light of the second wavelength which passes through the aperture plate and is selected spectral filter.

The optical system may include a continuous geometrical axis G, which does not run through the sample, on which the optical arrangement, the second focal point, the aperture plate, the spectral filter, and the detector—together with the mirror and the deflection element—are positioned, this geometrical axis G being at least partially identical to the optical axis in the region between the mirror and the detector.

The present invention according to the first aspect also provides that:
- the table is additionally movable in the direction of the Y spatial axis, X and Y axes lying at least approximately parallel to the surface of the sample holder.
- the deflection element includes a highly reflective region, intended for the laser beam, for deflecting the light from the first laser onto this mirror in a direction parallel to the optical axis, and in its remaining regions is essentially transparent to the light of both the first wavelength and the second wavelength.
- the highly reflective region of the deflection element is positioned at a distance A to the optical axis, which is identical to the geometrical axis G, so that the beam path for the light of the first wavelength coming out of the laser runs parallel and at the distance A to these axes.
- an opaque screen—for intermittent masking of a laser beam used for focusing and excitation and reflected from the sample—is positioned between the deflection element and the optical arrangement.
- the system additionally includes a separating element for separating the light of the first wavelength coming out of the laser into an excitation beam and a focusing beam, which is parallel to this excitation beam.
- an opaque screen—for intermittent masking of a laser beam used for exciting the fluorescent pigments—is positioned between the deflection element and the separating element.
- the first spectral filter is positioned between the aperture plate and the first detector.
- the system includes:
  - a second laser, which—to excite second fluorescent pigments—emits light of a third wavelength running parallel to the light of the first wavelength, so that these fluorescent pigments emit light of a fourth wavelength;
  - a second spectral filter for selecting a component of the light of the fourth wavelength; and
  - a second detector for measuring the intensity of the part of the light of the fourth wavelength selected by the second spectral filter,
  - characterized in that it additionally includes a beam splitter element, which is at least partially transparent to the light of the second wavelength emitted by the first fluorescent pigments and collimated by the optic, and which is implemented for reflecting and/or deflecting the light of the fourth wavelength from the geometric axis G in the direction of a second detector.
- the system additionally includes at least one convergent lens for collecting the light of the second wavelength and/or fourth wavelength passing through the aperture plate.
- the beam splitter element is positioned between the aperture plate and the detector.
- the sample holder which may be received by the sample table is implemented as a slide, particularly made of plastic, glass, silicon, pyrolytic graphite, and the like.
- the sample holder which may be received by the sample table is implemented as a microplate, particularly having 96, 384, 1536, or more wells.
- the sample holder which may be received by the sample table is implemented as a frame for receiving and holding multiple slides, particularly made of plastic, glass, silicon, pyrolytic graphite, and the like, and has the external dimensions of a microplate.
- the unit—during the excitation and measurement of the fluorescence emitted by the samples—may be fixed and the sample table is simultaneously implemented as movable in the direction of the X and/or Y axes, the Y axis running parallel to the axes.
- the sample table—for excitation and measurement of the fluorescence emitted by the samples—is implemented as movable in the direction of the X axis and the unit is simultaneously movable back and forth in the direction of the Y axis, the Y axis running parallel to the axes.

the oscillating linear drive is implemented as a "voice coil".

the unit also includes a counter-oscillator which—to absorb oscillations of the unit—is movable counter to the linear drive in the direction of the Y axis.

the aperture plate is implemented as replaceable for various aperture sizes.

the first spectral filter is implemented as a filter slider having at least two different filters which may be automatically replaced with one another filter filter slider is implemented so it may be manually replaced by another filter slider.

the beam splitter element is implemented as a carriage slider having replaceable mirrors.

the system includes a computer or microprocessor for recording and processing the measurement signals detected by detectors and for outputt data corresponding to these signals.

the computer or microprocessor is additionally implemented for controlling the movements of the table, the table being implemented as displaceable in the directions of the X and/or Y and/or Z axes and tiltable around the X and/or Y axes.

According to a second aspect, this object is achieved by an optical system having a continuous geometrical axis G which does not run through the sample, on which the optical arrangement, the second focal point, the aperture plate, the spectral filter, and the detector—together with the mirror and the deflection element—are positioned, this geometrical axis G being at least partially identical to the optical axis in the region between the mirror and the detector.

The present invention according to the second aspect also provides that:

using the deflection element, which includes a highly reflective region intended for the laser beam and is essentially transparent to the light of both the first wavelength and the second wavelength in its remaining regions, light from the first laser is deflected onto this mirror in a direction parallel to the optical axis.

the highly reflective region of the deflection element is positioned at a distance A to the optical axis, which is identical to the geometrical axis G, so that the beam path for the light of the first wavelength coming out of the laser 1 runs parallel and at the distance A to these axes.

to define an optimum Z position of the movable table and/or a sample, an opaque screen, positioned between the deflection element and the optical arrangement, is pulled out of the beam path and in which—on the basis of a series of measurement signals generated during a Z movement of the table by the first detector and recorded in a computer or microprocessor—the Z position of the table corresponding to the maximum of these measurement signals is calculated and the table is moved into this Z position.

the geometric center between the points of inflection of the rising and falling slopes of the measurement signal is taken to fix the maximum of these measurement signals.

defining an optimum Z position of the movable table and/or a sample is performed at at least three points of a sample holder and the table—in accordance necessary in the directions of the X, Y, and Z axes and tilted around the X and Y axes.

defining an optimum Z position of the movable table and/or a sample is performed using a computer or microprocessor, which detects and processes the measurement signals generated by detectors, outputs data corresponding to these signals, and additionally controls the movements of the table.

the table—before the measurement of the fluorescence on and/or in at least one sample—is displaced in the direction of the X and/or Y axes and is stopped for the excitation and measurement of the fluorescence—while simultaneously fixing the unit.

the table—during the excitation and measurement of the fluorescence on and/or in at least one sample and while simultaneously fixing the unit—is displaced in the direction of the X and/or Y axes.

for exciting and measuring the fluorescence on and/or in at least one sample—while simultaneously oscillating the unit in the direction of the Y axis—the table is fixed or displaced linearly in the direction of the X axis.

the corresponding detector signals are recorded and processed in the computer or microprocessor.

the opaque screen is pushed into the beam path and/or removed therefrom.

the excitation and measurement of the fluorescence on and/or in a sample is performed at a Z position of the movable table, sample holder, and/or a sample optimized and the corresponding detector signals are recorded and processed in the computer or microprocessor.

only one light flash and/or a few discrete light flashes per sample are emitted to excite the fluorescence.

multiple lasers are used for generating excitation light of different wavelengths in or on multiple fluorescent pigments and multiple detectors are used for measuring the corresponding signals.

signals of at least two lasers, fluorescent pigments, and detectors are recorded, processed, and output superimposed.

According to a third, and particularly preferred aspect, this object is achieved by an optical system for exciting and measuring fluorescence on or in samples treated using fluorescent pigments, including:

at least one first laser which emits light of a first wavelength to excite first fluorescent pigments, so that these first fluorescent pigments emit light of a second wavelength;

a deflection element that is implemented to separate an excitation beam of the first wavelength from a fluorescent light of the second wavelength;

a mirror, for deflecting the bundled light of the first wavelength, which comes out of the first laser and is incident on the mirror, in the direction of a sample or for deflecting light of the second wavelength, originating from the sample and being incident on the mirror, in the direction to a detector;

an optic, for producing a first focal point on or in the sample for the bundled light of the first wavelength, which is incident from the first laser and is deflected by the mirror;

a unit, which includes the mirror and optic, the mirror and optic being positioned fixed in relation to one another in the unit and this unit being positioned so it is linearly movable back and forth and being mechanically connected to an oscillating linear drive, the optic additionally being implemented as a collimator for the light of the second wavelength emitted by the first fluorescent pigment on or in the sample and the mirror additionally being implemented for deflecting this collimated light diametrically opposite to the direction of incidence of the bundled light of the first wavelength;

a table for receiving sample holders for samples treated using at least one first fluorescent pigment;

an optical arrangement for imaging a second focal point using the light of the second wavelength emitted by the first fluorescent pigment, collimated by the optic, and deflected by the mirror;

an aperture plate, positioned in the second focal point, for masking light of the second wavelength, which is incident on this aperture plate at a distance from the focal point greater than a specific distance;

a first spectral filter for selecting a component of the light of the second wavelength passing through the aperture plate; and a first detector for measuring the intensity of the light of the second wavelength which passes through the aperture plate and is selected by the first spectral filter, wherein a focusing beam of the light, which is emitted by the laser and is deflected by the deflection element into the direction of the mirror, is arranged to extend off-center and in a distance A to an optical axis of this optical system.

A preferred variant to this optical system is defined in that the oscillating linear drive comprises a connecting rod for linearly moving back and forth the unit.

According to a fourth, and particularly preferred aspect, this object is achieved by a method of exciting and measuring fluorescence on or in samples treated with fluorescent pigments and using an optical system. The method comprising the steps of:

exciting fluorescent pigments with a first laser that emits light of a first wavelength, so that these fluorescent pigments emit light of a second wavelength;

separating an excitation beam of the first wavelength from a fluorescent light of the second wavelength using a deflection element;

utilizing a mirror for deflecting the bundled light of the first wavelength, which comes out of the first laser and is incident on the mirror, in the direction of a sample, or for deflecting light of the second wavelength, originating from the sample and being incident on the mirror, in the direction to a detector;

producing a first focal point for the bundled light of the first wavelength, which is incident from the first laser and is deflected by the mirror, using an optic;

linearly moving a unit back and forth along an optical axis, the unit including the mirror and the optic that are positioned fixed in relation to one another in the unit, the unit being mechanically connected to an oscillating linear drive, the optic additionally being implemented as a collimator for the light of the second wavelength emitted by the first fluorescent pigments on or in the sample, and the mirror additionally being implemented for deflecting this collimated light of the first wavelength;

receiving with a table a sample holder for samples treated using at least one first fluorescent pigment;

imaging a second focal point with the light of the second wavelength that is emitted by the fluorescent pigments, collimated by the optic, and deflected by the mirror;

positioning an aperture plate in the second focal point for masking light of the second wavelength that is incident on this aperture plate at a distance from the focal point greater than a specific distance;

selecting a component of the light of the second wavelength that passes through the aperture plate with a first spectral filter; and measuring the intensity of the light of the second wavelength transmitted by the aperture plate and selected by the first spectral filter with a first detector;

wherein a focusing beam of the light, which is emitted by the laser and is deflected by the deflection element into the direction of the mirror, is arranged to extend off-center and in a distance A to an optical axis of this optical system.

A preferred variant to this method is defined in that the unit is linearly moved back and forth with a connecting rod of the oscillating linear drive.

Additional preferred embodiments and additional inventive elements derive from the dependent claims.

BRIEF DESCRIPTION OF THE DRAWINGS

The present invention will now be described in greater detail on the basis of schematic illustrations, which merely represent preferred examples of embodiments and do not restrict the scope of the disclosure in regard to the present invention.

DETAILED DESCRIPTION OF THE INVENTION

Figure 1:
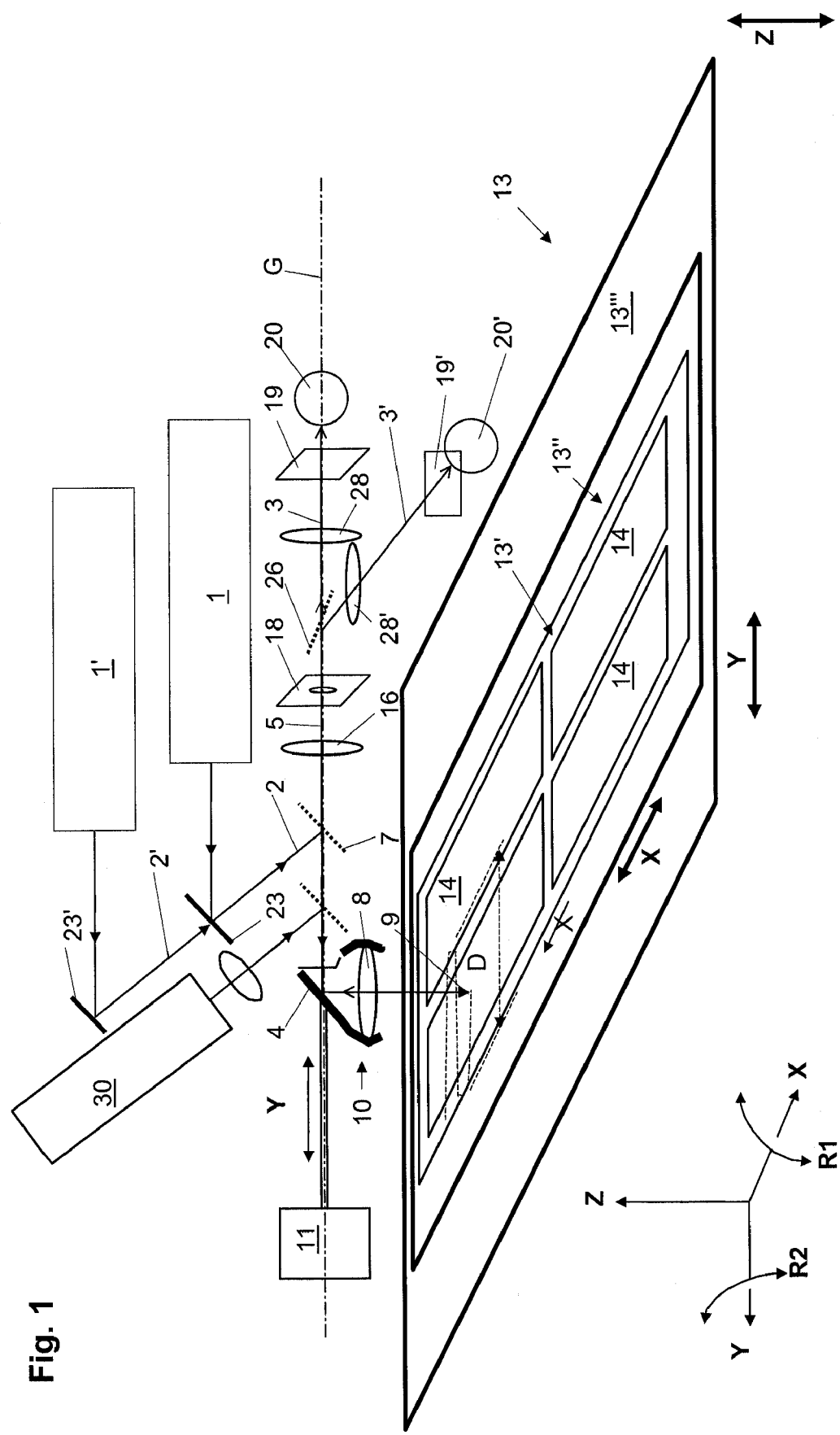
FIG. 1 shows a quasi-spatial schematic illustration of an optical system according to a first embodiment having two lasers.

FIG. 1 shows a quasi-spatial schematic illustration of an optical system of the reflection type according to a first embodiment. This optical system is preferably capable of exciting and measuring fluorescence on or in samples treated using fluorescent pigments and includes a first laser 1. This laser emits light of a first wavelength 2—to excite first fluorescent pigments—so that these first fluorescent pigments emit light of a second wavelength 3. A mirror 4 deflects the light of the first wavelength 2, which comes out of the first laser 1 and is incident on the mirror 4 parallel to an optical axis 5, in the direction of a sample 6 (cf. FIGS. 2 and 3). A deflection element 7 deflects the light 2 from the first laser 1 onto this mirror 4. An optic 8 produces a first focal point 9 for the incident light from the first laser 1 deflected by the mirror 4 of the first wavelength 2. A unit 10 includes the mirror 4 and the optic 8. This mirror 4 and the optic 8 are positioned fixed in relation to one another in the unit 10.

This unit 10 is positioned so it is movable back and forth linearly along the optical axis 5 and is mechanically connected to an oscillating linear drive 11. The oscillating linear drive 11 may be implemented, for example, as a stack of piezo elements; as a mechanical drive, including a connecting rod, for example, or as a naturally oscillating solid body excited by ultrasound waves. However, the implementation of an oscillating linear drive 11 as a "voice coil", as is described in U.S. Pat. No. 5,260,569 and particularly in U.S. Pat. No. 5,880,465, is preferred. In this case, a device is used to produce the back and forth movement which essentially corresponds to a loudspeaker, the membrane movements being tranferred to the unit 10 using a mechanical connection. This optic 8 is implemented accordingly, so that it additionally acts as a collimator for the light of the second wavelength 3 emitted by the first fluorescent pigments ("light originating from the sample"). The mirror 4 additionally deflects this collimated light 12 diametrically opposite to the direction of incidence of the light of first wavelength 3 and parallel to the optical axis 5.

This optical system additionally includes a table 13, movable at least in the direction of the X and Z spatial axes, for samples 6 treated using at least one first fluorescent pigment and for aligning the sample 6 in relation to the first focal point 9. The table 13 is preferably additionally movable in the direction of the Y spatial axis, the X axis and the Y axis running at least approximately parallel to the surface 15 of a sample holder 14. The X, Y, and Z spatial axes are at least approximately perpendicular to one another, the Y axis extending parallel to a horizontally running part of the optical axis 5 and to the geometrical axis G, which also runs horizontally.

The table 13 is preferably constructed in multiple parts and includes a part 13', movable in the direction of the X axis over a smaller distance (thin arrow), a part 13", movable in the direction of the X axis over a larger distance (thicker double arrow), and a part 13''', movable in the direction of the Y axis over a larger distance (thicker double arrow). The entire table 13' is movable in the direction of the Z axis. Electric motors are preferably used for moving the parts of the table 13.

Slides made of glass, for example, as have been known from light microscopy for a long time, are suitable as sample holders 14. Other and/or similar sample holders may be produced from plastic. Still other, essentially flat sample holders, which are also suitable for scanning tunnelling microscopy, for example, may be implemented from silicon or pyrolytic graphite and the like and/or include these materials. Sample holders may also be used which have a defined partitioning on the surface. This partitioning may include a uniform, grooved division; however, it may also have an array of depressions. Examples of sample holders having such an array of depressions are silicon or glass plates having multiple etched depressions. Further examples are standard microtitration plates (trademark of Beckman Coulter, Inc., 4300 N. Harbour Blvd., P.O. Box 3100 Fullerton, Calif., USA 92834) or "microplates", which include 96, 384, 1536, or more depressions in the form of "wells".

While dry or at least partially dried or immobilized samples are preferably prepared for investigation on slides, sample holder 14 having depressions and/or wells may accommodate liquid samples 6 or samples 6 located in a liquid. A frame 31 which essentially has the external dimensions of a microplate has been shown to be especially suitable for use in the optical system according to the present invention. This frame therefore fits in and/or on the same sample table 13 as a microplate and may also be placed there or removed therefrom automatically like a microplate, i.e., using a robot arm. This frame 31 is implemented for receiving and holding multiple slides, particularly made of plastic, glass, silicon, pyrolytic graphite, and the like. The arrangement of 4 glass slides on such a frame has especially proven itself. In this case, the object carriers 14 are arranged, as shown in FIG. 1, for example, in a row, long edge to long edge each pushed together or at a slight distance to one another (cf. FIG. 1). The frame 31 is preferably produced from plastic in the injection molding method, through which the production price may be kept low and the dimensional precision may be kept high. This dimensional precision makes using such frames 31 in all possible devices for automated handling of microplates significantly easier. Of course, the frames 31 may also be equipped with the slides 14 and inserted into the optical system according to the present invention by hand. Frames 31 equipped with slides 14 additionally ease the further handling of slides secured in this way, which now no longer have to be grasped directly between the process steps to be performed in the devices for automated handling.

The optical system additionally includes an optical arrangement 16 for imaging a second focal point 17 using the light of the second wavelength 3 emitted by the first fluorescent pigments, collimated by the optic 8, and deflected by the mirror 4 ("light originating from the sample"). An aperture plate 18 positioned in the second focal point 17 is used for masking light of the second wavelength 3 which meets this aperture plate 18 at a distance greater than a specific distance from the focal point 17. This aperture plate 18 is preferably implemented as replaceable, so that using multiple diameters of this confocal aperture plate, the sharpness and/or the brightness of the second focal point may be increased or reduced as required. Especially in the event of extremely poor light conditions, a larger plate, which causes a reduction of the imaging sharpness, may be useful. A replaceable aperture plate 18 allows selection of different aperture diameters for adjusting the imaging in the second focal point 17 to the sample volume and/or to the desired penetration depth of the excitation beam into the sample and selection of the corresponding depth of field of the detector arrangement.

The optical system also includes a first spectral filter 19 for selecting a component of the light of the second wavelength 3 passing through the aperture plate 18 and a first detector 20 for measuring the intensity of the light of the second wavelength 3 transmitted through the aperture plate 18 and selected by the first spectral filter 19 ("light originating from the sample").

The optical system according to the present invention includes a continuous geometrical axis G, which does not run through the sample, on which the optical arrangement 16, the second focal point 17, the aperture plate 18, the first spectral filter 19, and the first detector 20 are positioned—together with the mirror 4 and the deflection element 7—this geometrical axisG being at least partially identicalto the opical axis 5 in the region between the mirror 4 and the first detector 20.

This joint arrangement on the geometrical axis G has the advantage that the scanning of the sample may be performed at high speed using a very simply constructed unit 10 movable back and forth. This unit 10 actually only includes the mirror 4 and the optic 8. The oscillation frequency is preferably 20 Hz, the oscillation amplitude D able to be up to 25 mm or more.

The light of the laser 1 placed distal from this unit 10 and also the light, originating from the sample, running parallel and diametrically opposite to that of the laser 1, represents a purely optical connection between the scanning part of the system and the excitation and measurement part of the system, so that no oscillations are transferred from the scanning or raster part to the measurement part of the system. In addition, this arrangement allows the bundled light 2 of the laser 1 to be fed directly into the optical system. The mirror 4 deflects the bundled laser beam 2 onto the optic 8, which in turn always deflects the resulting focal point onto the same point on the optical axis 5. This optical axis 5 preferably runs vertically between the mirror 4 and the sample 6. The opitical system, based on coupling a bundled laser beam, is subject to fewer light losses than those which feed and deflect a collimated light beam in order to obtain a first focal point.

In the system according to the present invention, the optical axis 5 is identical to the geometrical axis G along a part which preferably runs horizontally. In a direction parallel to these axes 5, G, a bundled laser beam is used to excite the sample, and a collimated beam having light originating from the sample is used in the direction diametrically opposite thereto. In this way, the deflection element 7, which is to diffract the laser beam 2 in the direction of the mirror 4, but which is to be transparent to the collimated light beam, may be a simple glass plate. Typically, approximately 4% of a light beam is reflected and approximately 96% is transmitted at a boundary surface glass/air. Antireflection coating increases the transmission if necessary and reduces the reflection of such a glass plate. This simple glass plate or disk replaces the more expensive polarization beam splitter known from U.S. Pat. No. 5,260,569 (see FIG. 1 therein, reference number 13) and quarter-wave plates (see FIG. 1 therein, reference number 18), which are necessary in the related art because a collimated light beam is used in both directions, each of which requires the entire surface of the mirror and filter.

Figure 2:
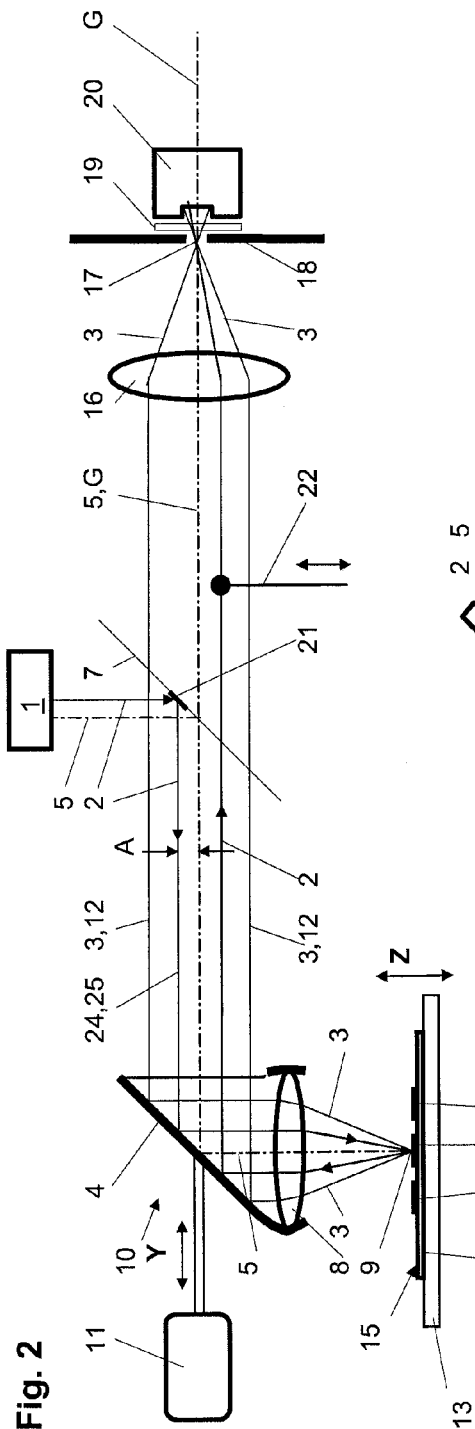
FIG. 2 shows a vertical partial section of an optical system according to a second embodiment having at least one laser.
Figure 3:
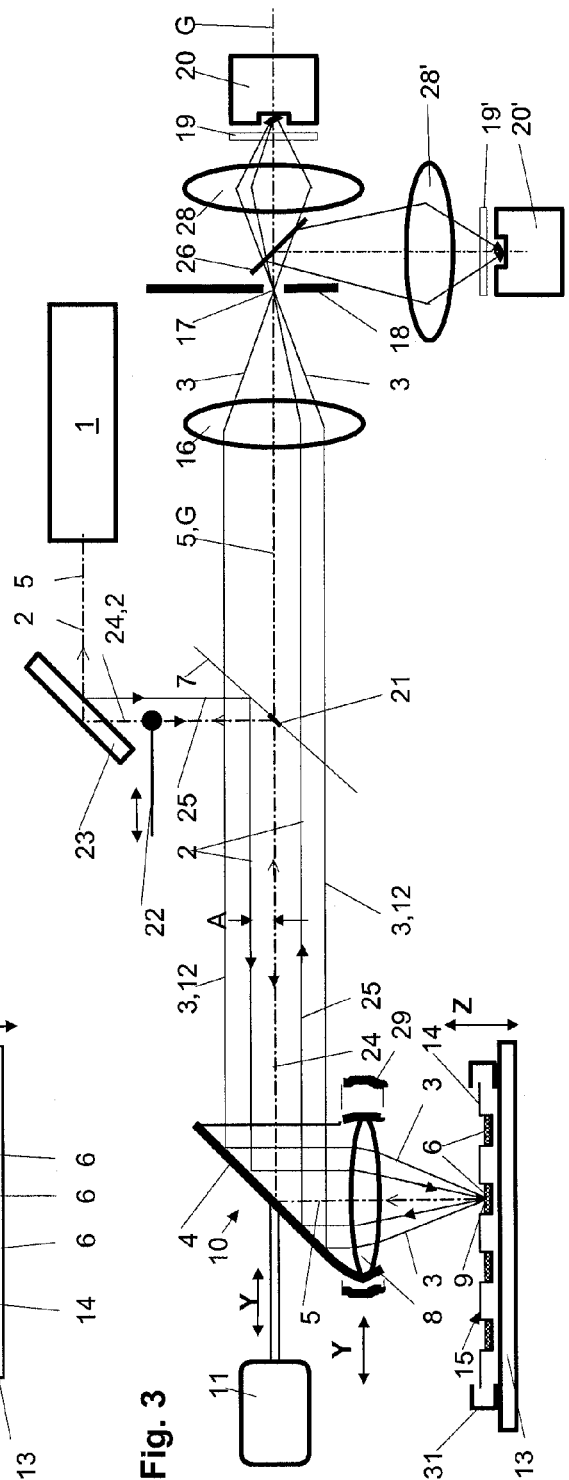
FIG. 3 shows a vertical partial section of an optical system according to a third embodiment having at least one laser.

A further advantage of the system according to the present invention is that the laser beam 2 for exciting the sample fluorescence must run parallel to the optical axis 5, but not in its center and not in the center of the geometrical axis G. This is advantageous above all for determining a mutually optimum Z position of sample 6 and first focal point 9. The laser beam then preferably runs at a distance (A) to the optical axis 5, which is identical to the geometrical axis G. Therefore, "off-center illumination" of the sample is possible, as is shown in FIGS. 2 and 3, for example.

Furthermore, the system according to the present invention includes the possibility of using a preferred deflection element 7, which, for deflecting the light 2 from the first laser 1 onto this mirror 4 in a direction parallel to the optical axis 5, includes a highly reflective region 21 intended for the laser beam 2 and is essentially transparent in its remaining regions to the light of both the wavelength 2 and the second wavelength 3. Therefore, if such a "pin mirror" is used, a greatly improved yield for the bundled laser light for exciting the fluorescence of the fluorescent pigments in or on the samples 6 results in comparison to the simple glass plate used as the deflection element 7. The loss of approximately 5% of the light originating from the sample and deflected on the highly reflective region 21 is not of great importance here.

In order to make the device more compact, the optical system may additionally include a simple mirror for reflecting the light beams running between the deflection element 7 and the mirror 4 (not shown). This simple mirror is then also positioned in the geometrical axis (G). However, in this case the optical arrangement 16, the second focal point 17, the aperture plate 18, the first spectral filter 19, and the first detector 20—corresponding to the deflection by the simple mirror—are positioned on a geometric axis G', which is different from G.

The optical system shown in FIG. 1, having two preferably monochromatic lasers of different wavelengths, additionally includes a second lase 1', which—to excite second fluorescent pigments—emits light of a third wavelength 2' running parallel to the light of the first wavelength 2, so that these fluorescent pigments emit light of a fourth wavelength 3'. A second spectral filter 19' selects a component of the light of the fourth wavelength 3' and a second detector 20' measures the intensity of the part of the light of the fourth wavelength 3' selected by the second spectral filter 19'. In addition, a beam splitter element 26 is provided, which is at least partially transparent to the light 12 of the second wavelength 3 emitted by the first fluorescent pigments and collimated by the optic 8 and which is implemented for reflecting and/or deflecting the light of the fourth wavelength 3' from the geometric axis G in the direction of a second detector 20'. This beam splitter element 26 may be designed as a dichroic mirror or even, for example, as a 50% beam splitter.

An object illuminator 30 in the form of a simple lamp, for example, is preferably also provided distal from the unit 10, so that the objects to be scanned may be observed and/or imaged using light optics if necessary. The light used is fed using a dichroic mirror positioned on the axes 5, G. The spectral filters 19, 19' are designed in such a way that they filter out this light. A separate detector (not shown) may be provided in order to capture the visual image of the samples 6. Alternatively, the detector 20 may also be used in order to scan the samples in the fluorescence mode, for example.

FIG. 2 shows a vertical partial section of an optical system for exciting and measuring fluorescence on or in samples treated using fluorescent pigments according to a second embodiment. For this second, somewhat simpler embodiment, only one monochromatic laser 1 is provided. The table 13 is additionally movable in the direction of the Y spatial axis, X and Y axes running at least approximately parallel to the surface 15 of a sample holder 14. The sample holders described in FIG. 1 may all also be used in this embodiment.

The deflection element 7, for deflecting the light 2 from the first laser 1 onto this mirror 4 in a direction parallel to the optical axis 5, includes a highly reflective region 21 intended for the laser beam 2. In its remaining regions, the deflection element 7 is essentially transparent to the light of both the first wavelength 2 and the second wavelength 3. The highly reflective region 21 of the deflection element 7 is positioned at a distance A to the optical axis 5, which is identical to the geometrical axis G, so that the beam path for the light of the first wavelength 2 coming out of the laser 1 runs parallel and at a distance A to these axes 5, G.

An opaque screen 22 is positioned between the deflection element 7 and the optical arrangement 16 for intermittent masking of a laser beam, used for focusing and excitation and reflected by the sample 6. In the state shown, this screen 22 is pushed into the beam path.

The bundled light 2 coming from the laser 1 is deflected on the highly reflective region 21 of the deflection element 7 in the direction of the mirror 4—preferably slanted at 45+ to the horizontal—parallel to the axes 5, G and at a distance A to these axes. The mirror 4 deflects this bundled laser beam 2 parallel and at the distance A to the now at least approximately vertically running optical axis 5, upon which the laser beam is deflected into the focal point 9 lying in the optical axis 5. The previously described course of the laser beam 2 is used for focusing, i.e., for fixing an optimum operating distance between optic 8 and sample 6. At the same time, the mutual position of focal point 9 and sample 6 is determined and set (as described below). The focusing beam 25 concentrated on the focal point 9 has a spot diameter between the diffraction limit and 2 mm. A preferred spot diameter is less than 15 μm. The focusing beam 25 is reflected by the sample and, at a distance from the optical axis 5, reaches the mirror 4 again, which deflects this reflected beam in the direction parallel to the horizontally running axes 5, G.

This off-center illumination is especially suitable for determining an exact operating distance—which is preferably up to 7 mm, but may also be more or less—because the laser beam is incident on the sample at an angle less than 90°. It is obvious that as the angle of incidence is reduced, the precision and/or the resolution in the direction of the Z axis increases, while an angle of incidence of 90° allows the lowest resolution in the direction of the Z axis, because under certain circumstances it may not be determined, for example, at what depth the focal point 9 is located inside the sample 6. In addition to this, the resolution of the optical system in the direction of the Z axis increases with increasing distance A. The reflected beam running parallel to the axes 5, G is deflected by an optical arrangement 16 into the second focal point 17, where it passes through the aperture plate 18. The spectral filter is now preferably pulled out of the beam path or replaced by a neutral density filter (gray filter), so that the reflected beam is incident on the detector 20 and the detector may measure the intensity of the reflectived beam.

If the optimum operating distance is not to be set using the reflection, but rather on the basis of the intensity of the fluorescence excited in the sample(s) and/or on the basis of diffuse scattered light generated in or on the sample 6, the screen 22 is pushed into the beam path (cf. FIG. 2) and the spectral filter 19 and/or a neutral density filter (gray filter) is placed in front of the detector 20. The bundled laser beam 1 is then used as the excitation beam 24, which is deflected into the first focal point 9 in the same way as the focusing beam 25. A part of the fluorescence, which propagates essentially in a dome shape from the sample 6, is collimated (i.e., aligned in parallel) in the optic 8 and deflected by the mirror 4 in the direction of the optical arrangement 16. In spite of a small loss, which is essentially determined by the area of the highly reflective region 21 of the deflection element 7 and the screen 22, this collimated fluorescent light is incident at the optical arrangement 16 and is focused in the second focal point 17. There—depending on the diameter of the aperture plate 18 selected—a certain part of the focused fluorescent light passes through this aperture plate 18 and the spectral filter 19 and is detected by the detector 20. The same beam path as just described is used for scanning the sample.

The first spectral filter 19 is positioned between the aperture plate 18 and the first detector 20. It may also be used as a window in the detector 20. However, the implementation of the first spectral filter 19 as a filler slider having, for example, five different filters which may be automatically replaced with one another is preferred, this spectral filter 19 being manually replaceable by another filter slider having another filter set.

This optical system preferably includes a computer or microprocessor for recording and processing the measurement signals detected by the detector 20 and for outputting data corresponding to these signals. This computer or microprocessor is preferably also implemented for controlling the movements of the table 13. The table 13, which is displaceable in the directions of the X and/or Y and/or Z axes, is preferably also implemented so it may be tilted around the X and/or Y axes.

According to the method according to the present invention, such an optical system is provided with a continuous geometrical axis G, which does not run through the sample. The optical arrangement 16, the second focal point 17, the aperture plate 18, the first spectral filter 19, and the first detector 20—together with the mirror 4 and the deflection element 7—are positioned on this geometrical axis G. In this case, this geometrical axis G is at least partially identical to the optical axis 5 in the region between the mirror 4 and the first detector 20.

During the excitation and measurement of the fluorescence emitted by the sample 6, the unit 10 of this optical system is fixed according to a first type of use. The sample table 13 is simultaneously moved in the direction of the X and/or Y axes, the Y axis running parallel to the axes 5, G. Using this table movement, which may be performed by the parts 13' (X movement) and 13''' (Y movement), for example, a linear scan on or in the samples 6 is made possible with continuous excitation and measurement, and a point scan is made possible with point excitation and point measurement.

During the excitation and measurement of the fluorescence emitted by the sample 6, the unit 10 of this optical system is moved back and forth in the direction of the Y axis according to a second type of use. The sample table 13 is simultaneously fixed and/or moved in the direction of the axis. Using only these movements of the unit 10, a linear scan on or in the samples 6 is made possible with continuous excitation and measurement, and with simultaneous movement of unit 10 (Y movement) and table 13 (movement of the part 13' results in X movement) an area scan is made possible with continuous excitation and measurement. The Y axis runs parallel to the axes 5, G in this case. The oscillating linear drive 11 for the unit 10 is preferably implemented as a "voice coil".

Before the effective scanning (measurement) of the samples, the Z position of the sample holder is set.

Laser pulses or lamp flashes may be used as an alternative light source for the excitation of the fluorescence. Discrete, individual laser pulses or discrete short series of a few laser pulses are then preferred, which excite the fluorescence at one point at a time in or on samples 6. Such point measurements are preferably performed especially during measurement of the fluorescence in samples provided in the 1536 wells of a high-density microplate, for example. Between or during the measurements, unit 10 and sample holder 14 are displaced in relation to one another in this case, the displacement of the unit 10 in the direction of the Y axis above all able to be performed extremely rapidly. The measurement of the fluorescence in these 1536 wells, which lasts approximately 1 minute in area scan with continuous excitation and measurement using the most rapid current devices, may thus be shortened to approximately 10 seconds. For microplates having even more wells or an even smaller scanning dimension, an even larger time savings results.

For samples 6 immobilized on essentially flat sample holders 14, for example, the opaque screen 22, which is positioned between the deflection element 7 and the optical arrangement 16, is pulled out of the beam path to define an optimum Z position of the movable table 13 and/or a sample 6. Subsequently—on the basis of a series of measurement signals generated during a Z movement of the table 13 by the first detector 20 and recorded in a computer or microprocessor—the Z position of the table corresponding to the maximum of these measurement signals is calculated and the table 13 is moved into this Z position. The geometric center between the points of inflection of the rising and falling slopes of the measurement signal is preferably taken to fix the maximum of these measurement signals. This method is preferably performed at at least three points of the sample holder and the table 13 is displaced—in accordance with the defined maxima for these three points—in the directions of the X, Y, and Z axes and tilted around the X and Y axes as far as necessary. It is advantageous if this definition of an optimum Z position is performed using a computer or microprocessor, which detects and processes the measurement signals generated by the detector 20, outputs data corresponding to these signals, and also controls the movements of the table 13.

FIG. 3 shows a vertical partial section of an optical system for exciting and measuring fluorescence on or in samples treated using fluorescent pigments according to a third embodiment. One or more preferably monochromatic lasers 1, 1' may be provided for this third embodiment. The table 13 is preferably movable in the direction of the X, Y, and Z spatial axes, X and Y axes running at least approximately parallel to the surface 15 of a sample holder 14. In addition, the table 13 may preferably be tilted around the X and/or Y axes. The sample holders described in FIGS. 1 and 2 may all also be used in this embodiment.

The deflection element 7 for deflecting the light 2 from the first laser 1 onto this mirror 4 in a direction parallel to the optical axis 5 includes a highly reflective region 21 intended for the laser beam 2. In its remaining regions, the deflection element 7 is essentially transparent to the light of both the first wavelength 2 and the second wavelength 3. The highly reflective region 21 of the deflection element 7 is positioned in the center of the optical axis 5, which is identical to the geometrical axis G, so that the beam path for the light of the first wavelength 2 coming out of the laser 1 runs parallel to and in the center of these axes 5, G.

This optical system includes a separating element 23 for separating the light of the first wavelength 2 coming out of the laser 1 into an excitation beam 24 for the fluorescence and a focusing beam 25 parallel to this excitation beam 24. An opaque screen 22 is positioned between the deflection element 7 and the separating element 23 for intermittent masking of a laser beam used to excite the fluorescence. This separating element 23 may be implemented as a simple, plane-parallel glass plate having complete mirroring on the back, if only one laser 1 is to be used.

The bundled light 2 from the laser 1 is reflected approximately 4% in the direction of the deflection element 7 on the non-mirrored first surface of the separating element 23. There, this laser beam is incident on a non-mirrored region and is again reflected approximately 4% and at a distance A paralle to the axes 5, G in the direction of the mirror 4. The bundled light 2 coming from the laser 1 is additionally reflected on the rear surface of the separating element 23. With a glass plate completely mirrored on the back, approximately 96% of the laser light 2 on optical axis 5 is deflected on the deflection element 7, where the light 2 is incident on its highly reflective region 21. The separating element 23 thus fulfills the object of separating the laser beam 2 into an excitation beam 24 running on the optical axis 5 and a focusing beam 25 running parallel thereto at a distance A.

A simple, plane-parallel glass plate which is placed diagonally in the beam path may also be used as an alternative separating element. The position of this plane-parallel glass plate is to be located between the laser 1 and the deflection element 7; however, this plane-parallel glass plate is preferably positioned between the laser 1 and the separating element 23 (not shown). The largest component of the laser beam passes through the glass plate with a slight parallel offset. rear boundary surface glass/air. A component of approximately 4% of the reflected beam then subsequently experiences another reflection at the front boundary surface. This leads to a small component of the laser light being deflected parallel to the main beam in the direction of the deflection element 7. In this case, the separating element 23 is implemented as a front surface mirror and is not used to separate the beam.

If two or more monochromatic lasers of different wavelengths are to be used, a plane-parallel plate implemented as a dichroic mirror is used as the separating element 23. Each laser may then—in accordance with the wavelenght of its light—be assigned its own separating element 23, 23', which is transparent to the remaining lasers. These separating elements are then preferably positioned on a shared optical axis and deflect the laser beams in the direction of one single deflection element 7, as may be seen from FIG. 1.

The bundled light 2, 2' coming from the lasers 1, 1' is deflected on the highly reflective region 21 of the deflection element 7 in the direction of the mirror 4—preferably slanted at 45° to the horizon The stronger of the two beams produced by the separating element 23 is therefore preferably incident on the highly reflective region 21 of the deflection element 7, where it is deflected, in the direction of the optical axis 5 and the geometrical axis G, identical thereto, onto the mirror 4. This excitation beam 24, which is preferably masked for focusing using inserted screen 22, is deflected by mirror 4 in the direction of the at least approximately vertically running optical axis 5, passes through the optic 8, and is incident on the sample 6 in the optical axis 5. The excitation beam 24, which is incident on the sample 6 at least approximately vertically, is especially suitable for exciting the fluorescence in sample 6 which are provided in the wells of microplates for investigation. Even if highdensity are preferably provided in the wells of microplates for investigation. Even if high-density microplates having not only 96, but 384, 1536, or more wells are to be used, the at least approximately vertical excitation beam always reaches the samples 6.

In contrast to the use of known and expensive, so-called "f(θ)-optics" for achieving an excitation beam which is incident on a sample 6 at least nearly perpendicularly, the present invention allows the use of significantly more cost-effective optical elements for the mirror 4 and the optis 8.

The second, preferably weaker light beam is thus incident on a non-mirrored region of the deflection element 7 where it is (approximately 4%) deflected, running parallel to the direction of the axes 5, G and at the distance A thereto, onto the mirror 4. This focusing beam 25 is preferably only active when screen 22 is inserted and is deflected by mirror 4 parallel and at a distance A to the direction of the at least approximately vertically running optical axis 5. The optic 8 deflects the focusing beam onto the focal point 9 lying in the at least approximately vertical optical axis 5.

The considerations of the use of the focusing beam (cf. second embodiment, FIG. 2) and of the focusing on the basis of the reflection, i.e., for fixing an optimum operating distance between optic 8 and sample 6, also essentially apply here. This is also true for focusing using measurement of the fluorescence and/or on the basis of diffuse scattered light generated in or on the sample 6, the screen 22 remaining pulled out of the beam path if the third embodiment described here is used and the fluorescence is measured.

A part of the fluorescence propagating essentially in a dome shape from the sample 6 is collimated (i.e., aligned in parallel) in the optic 8 and deflected by the mirror 4 in the direction of the optical arrangement 16. In spite of a small loss, which is essentially determined by the area of the highly reflective region 21 of the deflection element 7, this collimated fluorescent light is incident at the optical arrangement 16 and is focused in the second focal point 17. There, a certain part of the focused fluorescent light—depending on the selected diameter of the aperture plate 18—passes through this aperture plate 18 and the spectral filter 19 and is detected by the detector 20. The same beam path as just described is used for scanning the sample.

The excitation beam, which always runs in the optical axis 5 here, is reflected by the sample 6 and runs on the diametrically opposite path in the direction of the lasers 1,1'

If two monochromatic lasers 1, 1' are used, a beam splitter element 26 is preferably positioned between the aperture plate 18 and the first detector 20 (cf. FIG. 3). A first convergent lens 28 is used for collecting the light of the second wavelength 3 passing through the aperture plate 18. A second convergent lens 28' is positioned downstream from the beam splitter element 26, using which the light of the fourth wavelength 3' passing through the aperture plate 18 is collected and supplied to the second detector 20' having the second spectral filter 19'.

If necessary, further optical elements (lenses, mirrors, screens) may be placed between the aperture plate 18 and the detector 20—preferably between the spectral filter 19 and the detector 20—for optimized beam guiding in regard to signal yield and filter effect.

The reference numbers in the different figures each refer to identical features. Any arbitrary combinations of the embodiment shown and/or described are included in the scope of the present invention.

Advantages which differentiate the present invention from the related prior art include:
- the use of sample holders 14 the size of a microplate or even larger sample holders is made possible;
- the operating distance may be up to 7 mm or more;
- the numerical aperture of the objective is above a value of 0.4 and is up to 0.6 or more;
- the oscillation amplitude D may be up to 25 mm or more, in particular thanks to the use of a counter-oscillator 29;
- the at least approximately vertical excitation of the samples is achieved using a cost-effective and largely aberration-free optic;
- the deflection element 7 may be implemented as a simple glass disk or as a pin mirror and allows the separation of excitation beam and fluorescence as a simple optical element;
- the use of a deflection element 7 in the form of a pin mirror allows the simultaneous use of multiple monochromatic lasers of differing wavelengths and the measurement of a nearly unlimited number of different fluorescent pigments of differing emission wavelengths;
- the exchange of two monochromatic lasers of different wavelengths does not require any further modification of the optical system;
- the use of the different focusing modes disclosed in combination with an aperture plate of different aperture diameter allows greatly varying samples and sample formats to be brought into focus, excited, and their fluorescence measured.

What is claimed is:

1. An optical system, for exciting and measuring fluorescence on or in samples treated using fluorescent pigments, including:
   - at least one first laser which emits bundled light of a first wavelength to excite first fluorescent pigments, so that these first fluorescent pigments emit light of a second wavelength;
   - a deflection element that is implemented to separate an excitation beam of the first wavelength from a fluorescent light of the second wavelength;
   - a mirror, for deflecting the bundled light of the first wavelength, which comes out of the first laser and is incident on the mirror, in the direction of a sample or for deflecting light of the second wavelength, originating from the sample and being incident on the mirror, in the direction to a detector;
   - an optic, for producing a first focal point on or in the sample for the bundled light of the first wavelength, which is incident from the first laser and is deflected by the mirror;
   - a unit, which includes the mirror and optic, the mirror and optic being positioned fixed in relation to one another in the unit and the unit being positioned so it is linearly movable back and forth and being mechanically connected to an oscillating linear drive, the optic additionally being implemented as a collimator for the light of the second wavelength emitted by the first fluorescent pigment on or in the sample, and the mirror additionally being implemented for deflecting the collimated light diametrically opposite to the direction of incidence of the bundled light of the first wavelength;
   - a table for receiving sample holders for samples treated using at least one first fluorescent pigment;
   - an optical arrangement for imaging a second focal point using the light of the second wavelength emitted by the first fluorescent pigment, collimated by the optic, and deflected by the mirror;
   - an aperture plate, positioned in the second focal point;
   - a first spectral filter for selecting a component of the light of the second wavelength passing through the aperture plate; and
   - a first detector for measuring the intensity of the light of the second wavelength which passes through the aperture plate and is selected by the first spectral filter, wherein a focusing beam of the light, which is emitted by the laser and is deflected by the deflection element into the direction of the mirror, is arranged to extend off-center and in a distance A to an optical axis of the optical system.

2. The optical system of claim 1,
   wherein the oscillating linear drive comprises a connecting rod for linearly moving back and forth the unit.

3. The optical system of claim 1, wherein an excitation beam of the bundled light, which is emitted by the laser and deflected by the deflection element into the direction of the mirror, is additionally arranged to extend off-center and in a distance A to an optical axis of the optical system; or wherein an excitation beam of the bundled light, which is emitted by the laser and deflected by the deflection element into the direction of the mirror, is additionally arranged to extend identically to the focusing beam; or wherein an excitation beam of the bundled light, which is emitted by the laser and deflected by the deflection element into the direction of the mirror, is additionally arranged to extend centrically to the optical axis.

4. The optical system of claim 1, wherein the deflection element includes a highly reflective region that is provided for deflecting the bundled light of the first laser into the direction of the mirror and that the deflection element in its remaining regions is essentially transparent to the light of both the first wavelength and the second wavelength.

5. The optical system of claim 4, wherein the highly reflective region of the deflection element is arranged in a distance A to an optical axis so that the beam path of the bundled light of the first wave length that arrives from the laser extends in the distance A to the optical axis.

6. The optical system of claim 1, wherein the table is movable at least effectively in the direction of the X and Z spatial axes of an essentially rectangular coordinate system for aligning the sample in relation to the first focal point.

7. The optical system of claim 6, wherein the table for aligning the sample in relation to the first focal point in direction of the Z spatial axis is designed tiltable around the X and/or Y axes or linearly movable; or wherein the table is additionally movable in the direction of the Y spatial axis, the X and Y axes lying at least approximately parallel to the surface of the sample holder.

8. The optical system of claim 1, including an opaque screen for intermittent masking of an excitation beam and/or a focusing beam or of a respective laser beam that is reflected by the sample.

9. The optical system of claim 1, including a separating element for separating the bundled light of the first wavelength coming out of the laser into an excitation beam for exciting the fluorescence and a focusing beam, which is parallel to the excitation beam.

10. The optical system of claim 9, wherein the separating element is selected from a group consisting of a dichroic mirror, a plane-parallel glass plate having complete mirroring on the back, and a simple, plane-parallel glass plate, which is placed diagonally in the beam path.

11. The optical system of claim 1, including an off-set element that is arranged between the laser and the mirror and that is implemented as a plane-parallel glass plate, which is placed at an angle in the beam path.

12. The optical system of claim 1, wherein the first spectral filter is positioned between the aperture plate and the first detector.

13. The optical system of claim 1, including: a second laser, which, to excite second fluorescent pigments, emits bundled light of a third wavelength, so that these fluorescent pigments emit light of a fourth wavelength; a second spectral filter for selecting a component of the light of the fourth wavelength; and a second detector for measuring the intensity of the part of the light of the fourth wavelength selected by the second spectral filter, wherein the optical system additionally includes a beam splitter element, which is at least partially transparent to the light of the second wavelength emitted by the first fluorescent pigments and collimated by the optic, and which is implemented for reflecting and/or deflecting the light of the fourth wavelength into the direction of a second detector.

14. The optical system of claim 13, additionally including at least one convergent lens for collecting light of a second wavelength and/or a fourth wavelength passing through the aperture plate.

15. The optical system of claim 13, wherein the beam splitter element is positioned between the aperture plate and the detector.

16. The optical system of claim 1, wherein the sample holder, which is constructed to be received by the sample table, is implemented as a slide; or wherein the sample holder, which is constructed to be received by the sample table, is implemented as a microplate; or wherein the sample holder, which is constructed to be received by the sample table, is implemented as a frame for receiving and holding multiple slides, and has the external dimensions of a microplate.

17. The optical system of claim 1, wherein the sample table, for excitation and measurement of the fluorescence emitted by the samples, is implemented as movable in the direction of an X spatial axis, and wherein the unit is simultaneously movable back and forth in the direction of an Y spatial axis, the Y axis running parallel to the optical axis.

18. The optical system of claim 1, wherein the oscillating linear drive is implemented as a "voice coil".

19. The optical system of claim 1, wherein the unit also includes a counter-oscillator which, to absorb oscillations of the unit, is movable counter to the linear drive in the direction of an Y spatial axis.

20. The optical system of claim 1, wherein the aperture plate is implemented as replaceable for various aperture sizes.

21. The optical system of claim 1, wherein the first spectral filter is implemented as a filter slider having at least two different filters which are designed to be automatically replaceable with one another.

22. The optical system of claim 21, wherein the filter slider is implemented to be manually replaced by another filter slider.

23. The optical system of claim 1, including a computer or microprocessor for recording and processing the measurement signals detected by detectors and for outputting data corresponding to these signals.

24. The optical system of claim 23, wherein the computer or microprocessor is additionally implemented for controlling the movements of the table, the table being implemented as displaceable in the direction of an X and/or Y and/or Z spatial axis and tiltable around the X and/or Y axis.

25. A method of exciting and measuring fluorescence on or in samples treated with fluorescent pigments and using an optical system, comprising the steps of:
  exciting first fluorescent pigments with a first laser that emits bundled light of a first wavelength, so that these fluorescent pigments emit light of a second wavelength;
  separating an excitation beam of the first wavelength from a fluorescent light of the second wavelength using a deflection element;
  utilizing a mirror for deflecting the bundled light of the first wavelength, which comes out of the first laser and is incident on the mirror, in the direction of a sample, or for deflecting light of the second wavelength, originating from the sample and being incident on the mirror, in the direction to a detector;
  producing a first focal point for the bundled light of the first wavelength, which is incident from the first laser and is deflected by the mirror, using an optic;
  linearly moving a unit back and forth along an optical axis, the unit including the mirror and the optic that are positioned fixed in relation to one another in the unit, the unit being mechanically connected to an oscillating linear drive, the optic additionally being implemented as a collimator for the light of the second wavelength emitted by the first fluorescent pigments on or in the sample, and the mirror additionally being implemented for deflecting the collimated light diametrically opposite to the direction of incidence of the bundled light of the first wavelength;
  receiving with a table a sample holder for samples treated using at least one first fluorescent pigment;
  imaging a second focal point with the light of the second wavelength that is emitted by the first fluorescent pigments, collimated by the optic, and deflected by the mirror;
  positioning an aperture plate in the second focal point;
  selecting a component of the light of the second wavelength that passes through the aperture plate with a first spectral filter;
  and measuring the intensity of the light of the second wavelength transmitted by the aperture plate and selected by the first spectral filter with a first detector;

wherein a focusing beam of the light, which is emitted by the laser and is deflected by the deflection element into the direction of the mirror, is arranged to extend off-center and in a distance A to an optical axis of the optical system.

26. The method of claim 25, wherein the unit is linearly moved back and forth with a connecting rod of the oscillating linear drive.

27. The method of claim 25, wherein the bundled light of the first laser is deflected into the direction of the mirror using a highly reflective region that is provided by the deflection element, which in its remaining regions is essentially transparent to the light of both the first wavelength and the second wavelength.

28. The method of claim 25, in which:
second fluorescent pigments are excited using a second laser that emits bundled light of a third wavelength, so that these fluorescent pigments emit light of a fourth wavelength;
a component of the light of the fourth wavelength is selected using a second spectral filter; and
the intensity of the part of the light of the fourth wavelength selected by the second spectral filter are measured using a second detector,
wherein light of the fourth wavelength is reflected and/or deflected into the direction of a second detector using a beam splitter element of the optical system, the beam splitter element being at least partially transparent to the light of the second wavelength emitted by the first fluorescent pigments and collimated by the optic.

29. The method of claim 25, wherein the sample table is moved in the direction of an X spatial axis for excitation and measurement of the fluorescence emitted by the samples, and wherein the unit is simultaneously moved back and forth in the direction of an Y spatial axis, the Y axis running parallel to the optical axis.

30. The method of claim 25, wherein a counter-oscillator of the optical system is moved counter to the linear drive in the direction of an Y spatial axis to absorb oscillations of the unit.

31. The method of claim 25, wherein a series of measurement signals generated by the first detector during a Z movement of the table is recorded in a computer or microprocessor, and wherein the Z position of the table corresponding to these measurement signals is calculated to define an optimum Z position of the movable table and/or a sample and the table is moved into the optimum Z position.

32. The method of claim 31, wherein an opaque screen, positioned between the deflection element and the first laser or the aperture plate, is pushed into the beam path or is pulled out of the beam path when carrying out the series of measurement signals.

33. The method of claim 31, wherein the geometric center between the points of inflection of the rising and falling slopes of the measurement signal is taken to fix the optimum of the Z position.

34. The method of claim 31, wherein the method is performed at at least three points of a sample holder and the table in accordance with the defined maxima for these three points, and wherein the table is displaced in the directions of the X, Y, and Z axes and tilted around the X and Y axes.

35. The method of claim 31, which is performed using a computer or microprocessor, which detects and processes the measurement signals generated by the first detector, outputs data corresponding to these signals, and additionally controls the movements of the table.

36. The method of claim 25, wherein the table is displaced linearly in the direction of the X axis for exciting and measuring the fluorescence on and/or in at least one sample, the unit being simultaneously oscillated in the direction of the Y axis.

37. The method of claim 25, wherein multiple lasers are used for generating excitation light of different wavelengths in or on multiple fluorescent pigments and multiple detectors are used for measuring the corresponding signals.

* * * * *